(12) United States Patent
O'Brien et al.

(10) Patent No.: US 8,057,543 B2
(45) Date of Patent: Nov. 15, 2011

(54) STENT COATING FOR ELUTING MEDICATION

(75) Inventors: Robert C. O'Brien, Sykesville, MD (US); Christine A. Frysz, Marriottsville, MD (US)

(73) Assignee: Greatbatch Ltd., Clarence, NY (US)

( * ) Notice: Subject to any disclaimer, the term of this patent is extended or adjusted under 35 U.S.C. 154(b) by 160 days.

(21) Appl. No.: 11/307,226

(22) Filed: Jan. 27, 2006

(65) Prior Publication Data

US 2006/0200231 A1 Sep. 7, 2006

Related U.S. Application Data

(60) Provisional application No. 60/648,133, filed on Jan. 28, 2005.

(51) Int. Cl.
*A61F 2/02* (2006.01)
*A61F 2/06* (2006.01)

(52) U.S. Cl. .................. 623/11.11; 427/2.24; 623/1.44

(58) Field of Classification Search ................. 623/1.44, 623/1.42, 1.11; 427/2.1–2.31
See application file for complete search history.

(56) References Cited

U.S. PATENT DOCUMENTS

| | | | | |
|---|---|---|---|---|
| 4,236,994 A | * | 12/1980 | Dugdale | ................. 204/298.09 |
| 5,222,971 A | | 6/1993 | Willard et al. | |
| 5,607,463 A | | 3/1997 | Schwartz et al. | |
| 5,649,951 A | | 7/1997 | Davidson | |
| 5,824,056 A | | 10/1998 | Rosenberg | |
| 6,096,070 A | * | 8/2000 | Ragheb et al. | ............... 623/1.39 |
| 6,174,329 B1 | * | 1/2001 | Callol et al. | ................. 623/1.34 |
| 6,387,121 B1 | | 5/2002 | Alt | |
| 6,716,444 B1 | | 4/2004 | Castro et al. | |
| 6,764,505 B1 | | 7/2004 | Hossainy et al. | |
| 6,805,898 B1 | | 10/2004 | Wu et al. | |
| 6,820,676 B2 | | 11/2004 | Palmaz et al. | |

(Continued)

FOREIGN PATENT DOCUMENTS

EP 0 362 444 A1 11/1990

(Continued)

OTHER PUBLICATIONS

Richards P.J. et al., "Wind Loads on Porous Structures—its microenvironment and its effect on structural loads", Nov. 1999, Journal of Wind Engineering and Industiral Aerodynamics, vol. 83, No. 1, pp. 455-465.*

(Continued)

*Primary Examiner* — Thomas J Sweet
*Assistant Examiner* — Jason-Dennis Stewart
(74) *Attorney, Agent, or Firm* — Michael F. Scalise

(57) ABSTRACT

A vascular stent comprising a drug-eluting outer layer of a porous sputtered columnar metal having each column capped with a biocompatible carbon-containing material is described. This is done by placing the stent over a close-fitting mandrel and rotating the assembly in a sputter flux. The result is a coating that is evenly distributed over the outward-facing side of the stent's wire mesh while preventing the sputtered columnar coating from reaching the inward facing side where a smooth hemocompatible surface is required. The stent is then removed from the mandrel, exposing all surfaces, and finally coated with a layer of carbon such as amorphous carbon or diamond-like carbon. The carbonaceous coating enhances biocompatibility without preventing elutriation of a therapeutic drug provided in the porosity formed between the columnar structures. The result is a stent that is adapted to both the hemodynamic and the immune response requirements of its vascular environment.

17 Claims, 9 Drawing Sheets

U.S. PATENT DOCUMENTS

| | | |
|---|---|---|
| 6,821,624 B2 * | 11/2004 | Utsumi et al. ............... 428/408 |
| 6,830,747 B2 | 12/2004 | Lang et al. |
| 6,858,221 B2 | 2/2005 | Sirhan et al. |
| 6,908,624 B2 * | 6/2005 | Hossainy et al. ............ 424/424 |
| 7,208,011 B2 * | 4/2007 | Shanley et al. ............. 623/1.42 |
| 2001/0039449 A1 * | 11/2001 | Johnson et al. ............. 623/1.19 |
| 2003/0036794 A1 * | 2/2003 | Ragheb et al. .............. 623/1.15 |
| 2003/0068355 A1 * | 4/2003 | Shanley et al. .............. 424/426 |
| 2003/0088307 A1 | 5/2003 | Shulze et al. |
| 2003/0125800 A1 | 7/2003 | Shulze et al. |
| 2003/0144728 A1 | 7/2003 | Scheuermann et al. |
| 2003/0191354 A1 | 10/2003 | Grabowy |
| 2003/0225450 A1 | 12/2003 | Shulze et al. |
| 2004/0131700 A1 | 7/2004 | Cifra et al. |
| 2004/0148015 A1 | 7/2004 | Lye et al. |
| 2004/0172124 A1 | 9/2004 | Vallana et al. |
| 2004/0176828 A1 | 9/2004 | O'Brien |
| 2005/0038498 A1 | 2/2005 | Dubrow et al. |
| 2005/0038505 A1 | 2/2005 | Shulze et al. |
| 2005/0107870 A1 * | 5/2005 | Wang et al. ................. 623/1.44 |
| 2005/0187608 A1 * | 8/2005 | O'Hara ....................... 623/1.15 |
| 2006/0127443 A1 * | 6/2006 | Helmus ....................... 424/423 |

FOREIGN PATENT DOCUMENTS

| | | |
|---|---|---|
| EP | 1 454 651 A1 | 8/2004 |
| WO | WO 99/36193 | 7/1999 |
| WO | WO 2004/105826 A2 | 9/2004 |

OTHER PUBLICATIONS

Communication from European Patent Office, Extended Search Report, Patent Application No. 06001891.8, Aug. 29, 2006.

Richards P.J. et al., "Wind Loads on Porous Structures—its microenvironment and its effect on structural loads", Nov. 1999, Journal of Wind Engineering and Industrial Aerodynamics, vol. 83, No. 1, pp. 455-456.

* cited by examiner

STENT COATING FOR ELUTING MEDICATION

FIELD OF THE INVENTION

This invention relates to stents provided with coatings for eluting medication to prevent or lessen the severity of restenosis.

PRIOR ART

In order to minimize the response of surrounding tissue to the trauma of stent insertion and expansion, stent coatings must be biocompatible. A further requirement is that a stent coating must adhere to a substrate undergoing plastic deformation. This occurs during insertion and expansion of the stent into the vasculature system. Plastic deformation involves grain rotation and elongation, and intersection of slip planes with the substrate surface. The result is that on a scale below the grain size of the substrate, deformation is highly non-uniform, with some areas undergoing little or no deformation and others extreme deformation with associated increase in surface roughness and irregularity. Therefore, coating adhesion must be preserved through the deformation process.

Conventional stent coatings can be classified as being either passive or active. Passive coatings rely on biocompatible materials to minimize the body's response to placement of the stent into the vasculature. Generally recognized "passive" coating materials include carbon, iridium oxide, titanium, and the like, as disclosed in U.S. Pat. No. 5,824,056 to Rosenberg. U.S. Pat. No. 5,649,951 to Davidson discloses coatings of zirconium oxide or zirconium nitride.

Drug eluting or "active" coatings have proven more effective for the prevention of restenosis. Such stents generally comprise a surface polymer containing a therapeutic drug for timed release. A second coating may be added to extend the period of effectiveness by limiting the rate of drug diffusion from the first, drug-containing coating. This second coating may be a polymer, or a sputtered coating as described in U.S. Pat. No. 6,716,444 to Castro et al.

However, polymeric drug eluting coatings suffer from a number of disadvantages. First, they can have poor adhesion to the stent, especially while undergoing plastic deformation during insertion and expansion of the stent into the vasculature. Secondly, due to biocompatiblity/hemocompatibility issues some polymers actually contribute to restenosis. Finally, that part of the coating facing the inside of the vasculature lumen loses its medication content to the bloodstream with little beneficial effect.

U.S. Pat. No. 6,805,898 to Wu et al. attempted to overcome adhesion problems by introducing roughness to the vasculature-facing portion of the stent while leaving the blood-facing side in a polished condition for better hemocompatibility. Surface roughness was increased by means of grit blasting, sputtering, and the like. Not only did augmenting surface roughness improve adhesion between the polymer and the stent, it also allowed for a thicker polymer coating to be applied. However, the final stent configuration still had eluting polymer in contact with body tissue, allowing biocompatibility issues to persist.

U.S. Pat. No. 5,607,463 to Schwartz et al. carried out experiments in which it was shown that tissue response to polymers could be reduced by means of a barrier layer of tantalum and niobium thin films on the exposed polymer surfaces. Specifically, in vivo tests showed an absence of thrombosis, inflammatory response, or neointimal proliferation when a thin tantalum or niobium barrier layer covered a polymer. However, in the case of a drug eluting polymer, these coatings detrimentally isolated the drug from the tissue as well.

U.S. Patent Application Pub. No. 2004/0172124 to Vallana et al. optimized the coating configuration by limiting the drug-eluting material to only that portion of the stent surface in contact with the vasculature. This was done by confining the drug eluting polymer to outward facing channels which were micro-machined into the stent mesh elements. All other stent surfaces were coated with hemocompatible carbon. Thus, the use of a biocompatible-problematic carrier polymer was minimized, but not eliminated.

In addition, U.S. Pat. No. 6,820,676 to Palmaz shows that, independent of the stent's surface composition, the surface texture of the stent or coating has an effect on the ability of proteins to adsorb into the stent surface, ultimately allowing thrombosis formation. It was shown that the surface texture can be controlled by grain size and other means to prevent protein adsorption and subsequent thrombosis.

Thus, even though much work has been done to develop stent systems comprising drug eluting polymers while minimizing, and even eliminating, thrombosis, inflammatory response and neointimal proliferation, further improvements are required to fully realize these goals. The present stent coating is believed to accomplish just that.

SUMMARY OF THE INVENTION

In the present invention, the drug-eluting outer layer of a stent consists of a porous sputtered metal or ceramic coating rather than a conventionally deposited polymer. This is done by placing the stent over a close-fitting mandrel and rotating the assembly in a sputter flux. The result is a coating that is evenly distributed over the outward-facing side of the stent's wire mesh while preventing the sputtered coating from reaching the inward facing side where a smooth hemocompatible surface is required. The stent is then removed from its mandrel, exposing all surfaces, and finally coated with a layer of carbon such as amorphous carbon or diamond-like carbon. The carbonaceous coating enhances biocompatibility without preventing elution of the therapeutic drug. The result is a stent that is adapted to both the hemodynamic and the immune response requirements of its vascular environment.

These and other objects and advantages of the present invention will become increasingly more apparent by a reading of the following description in conjunction with the appended drawings.

BRIEF DESCRIPTION OF THE DRAWINGS

FIG. 2A is an enlarged cross-sectional view of the indicated portion of the stent wire 14 shown in FIG. 2 comprising a biocompatible porous columnar coating 16 supported on the stent wire 14 with a thin carbonaceous material 18 providing a cap on each of the columns as well as covering the inside-facing surface 14B of the wire.

FIG. 3A is an enlarged cross-sectional view of the indicated portion of FIG. 3.

DETAILED DESCRIPTION OF THE PREFERRED EMBODIMENTS

It has been found that coatings having a columnar structure can be made to adhere strongly to a substrate even while the substrate undergoes extensive plastic deformation. This is possible because the porous film consists of many strongly adhering individual columns rather than a single thin film coating. Furthermore, it has been shown that when thin columnar coatings are themselves coated with a biocompatible material such as carbon, the carbon continues the original columnar structure rather than disposing itself as a continuous non-porous barrier layer. This is described in U.S. Patent Application Pub. No. 2004/0176828 to O'Brien, which publication is assigned to the assignee of the present invention and incorporated herein by reference. These characteristics are put to use in the present invention as a medication-carrying structure on a stent for the purpose of eluting the medication into surrounding tissue to lessen or prevent restenosis.

Figure 1:
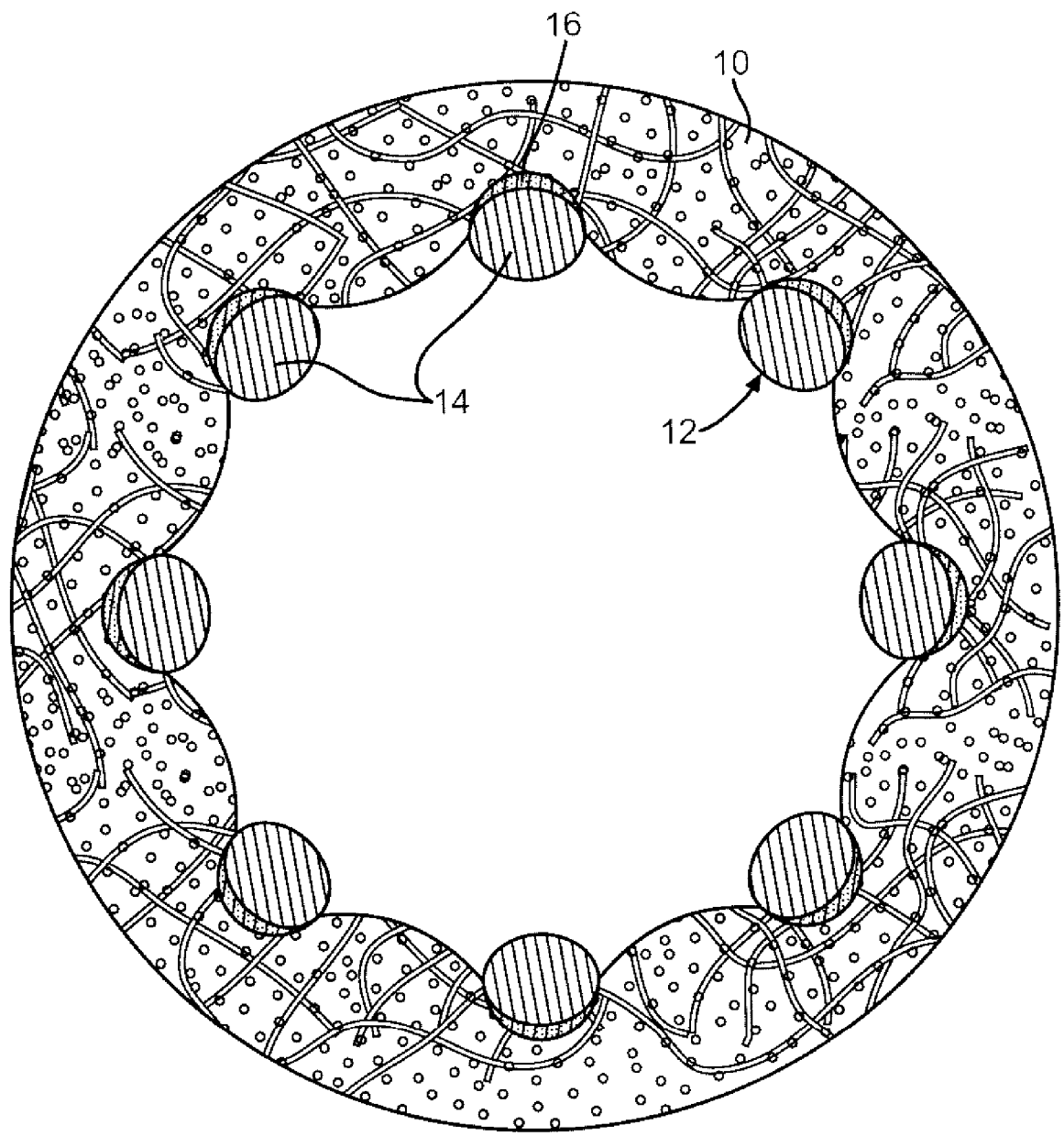
FIG. 1 is a cross-sectional view of a stent 12 supporting a blood vessel 10 according to the present invention.

Referring now to the drawings, FIG. 1 shows a cross-section of a blood vessel 10 with a stent 12 inserted and expanded therein. In the current invention, the medication eluting coating is limited to that portion of the stent in contact with tissue, which is exemplified by the blood vessel 10.

The stent 12 is comprised of a plurality of wires 14 forming an elongated hollow tube and disposed so as to be capable of circumferential expansion. Commonly used stent materials include platinum, Nitinol, and even medical grade 316L stainless steel containing about 16% nickel. The wires 14 provide for an elongated, expandable hollow tube that can, in a preferred embodiment, increase in diameter when the ends of the hollow tube are moved closer relative to each other and decrease in diameter when the ends are moved apart. A design objective is to have as little length change as possible when the stent is expanded. Physicians have a hard enough time lining up a stent with a lesion without it acting like an accordion.

The stent 12 is positioned in the vasculature of a patient during or after a procedure, such as an angioplasty, atherectomy, or other interventional therapy, and then expanded to an appropriate size (i.e., approximately the same diameter as the vessel 10 in the region where placed), thus supporting that vascular region. When in its expanded configuration, the stent 12 provides support to the vascular walls thereby preventing constriction of the vascular region in which it is located and maintaining the vascular lumen open. This is often referred to as maintaining vascular patency.

Figure 2:
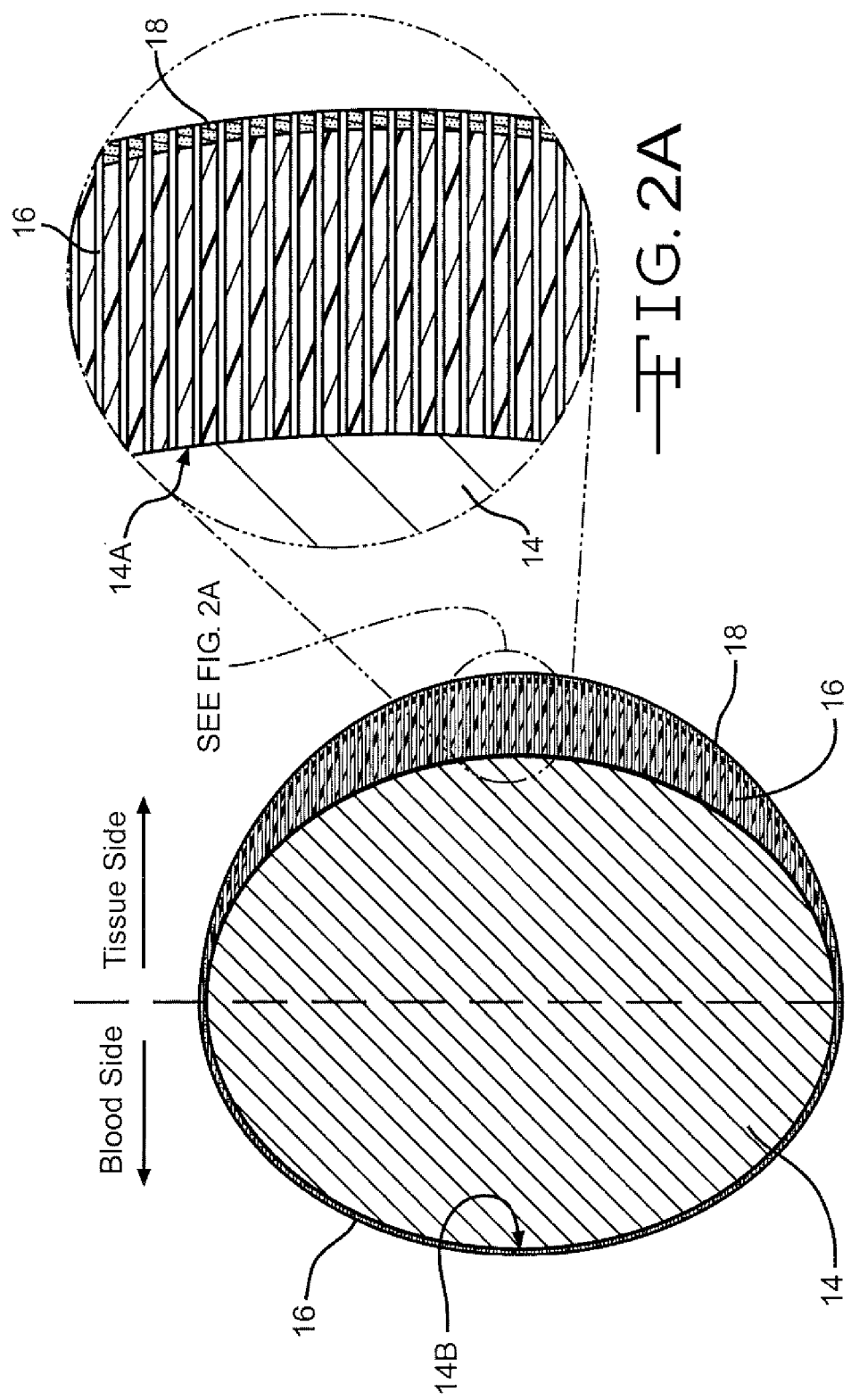
FIG. 2 is a cross-sectional view of a wire 14 comprising the stent 12 shown in FIG. 1.

FIG. 2 represents a cross-section of a wire 14 comprising the vascular stent 12. The stent wire 14 has a roughly circular cross-section comprising an outside-facing surface 14A and an inside-facing surface 14B. The outside-facing surface 14A of the stent wire faces the blood vessel wall and serves as a substrate provided with a coating 16 of columnar material to a thickness of about 0.1 µm to about 20 µm. Sputtering causes the columnar material to first be physically absorbed with some implantation into the wire material. This is due to the kinetic energy generated by the sputtering process prior to the column growing to its desired length.

While sputtering is a preferred method for depositing the columnar coating 16, other suitable thin film deposition method can be used. These include chemical vapor deposition, pulsed laser deposition, evaporation including reactive evaporation, and thermal spray methods. Also, while the wire 14 is shown having a circular cross-section, that is not necessary. Other embodiments of the stent 12 comprise wires 14 having triangular, square, rectangular, hexagonal, and the like cross-sections.

Figure 3:
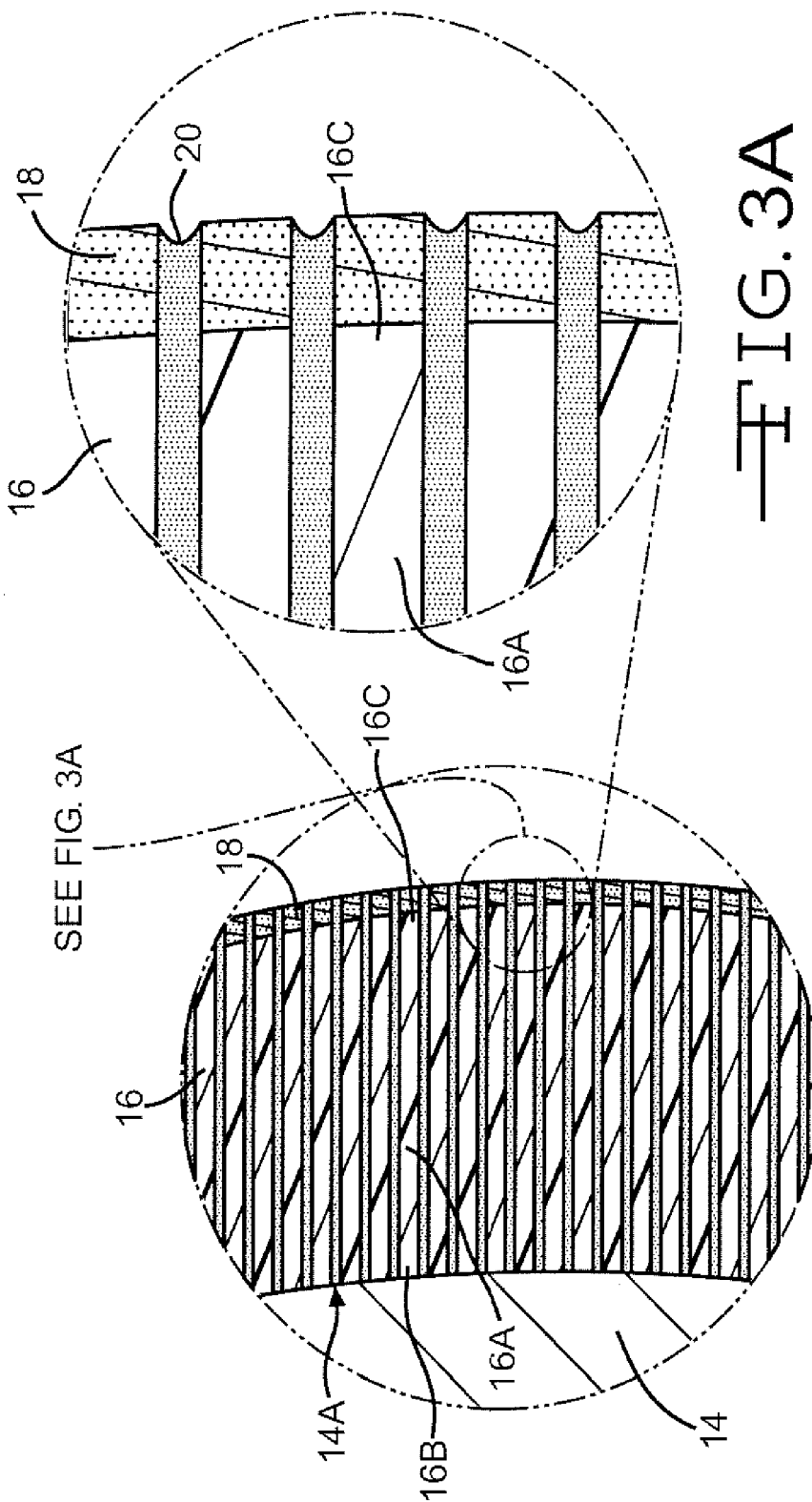
FIG. 3 is a cross-sectional view of the stent portion shown in FIG. 2A, but with the capillary spaces between the columnar coating 16 infused with a medication compound 20.

As shown in FIGS. 3 and 3A, each column of the coating 16 comprises an intermediate portion 16A extending to a base 16B adhered to the inside-facing surface 14B of the wire 14 and a tip 16C. Each column is of a relatively consistent cross-section along its length extending to the base 16B and tip 16C. That way, the columns are discrete members that only adhere to the wire substrate at their base 16B, but do not join to an immediately adjacent column. Titanium nitride is a preferred material for the columnar coating 16, although other useful materials include, but are not limited to, boron, aluminum, calcium, gold, hafnium, iridium, molybdenum, niobium, platinum, rhenium, ruthenium, silicon, silver, tantalum, titanium, tungsten, yttrium, and zirconium, and carbides, oxides, nitrides, oxynitrides, carbonitrides thereof.

To further lessen the response of contacted tissue to the presence of the stent 12, the inside-facing surface 14B of the wire 14 as well as each columnar tip 16C is coated with a carbonaceous material 18, such as amorphous carbon or diamond-like carbon. During this operation, the carbon 18 assumes the morphology of a "cap" adhered to each tip 16C of the porous columnar coating 16 supported on the outside-facing surface 14A of the stent wire 14. The carbon caps 18, which are also preferably provided by a sputtering process, are at a thickness of about 0.05 µm to about 2.0 µm. That is, the porosity of the drug-eluting columnar coating 16 is maintained. This is because while the thickness of the carbon cap is sufficient to impart biocompatibility to the columnar tip 16C, it is insufficient to form a continuous coating that could detrimentally isolate the drug eluting porosity inherent in the columnar structure. The carbon 18 that coats the bare metal inside-facing surface 14B of the stent wire 14 forms a smooth continuous pore-free layer suitable for contact with blood.

Finally, as shown in FIGS. 3 and 3A, the capillary spaces between the columns of the coating 16 and the carbon cap 18 are infused with medication 20 to inhibit restenosis. This can be done by various methods well known to those skilled in the art including spraying the stent with a medication solution, dipping the stent into a medication solution, immersing the stent in a medication solution under vacuum conditions and centrifuging the medication solution into the porosity.

Figure 4:
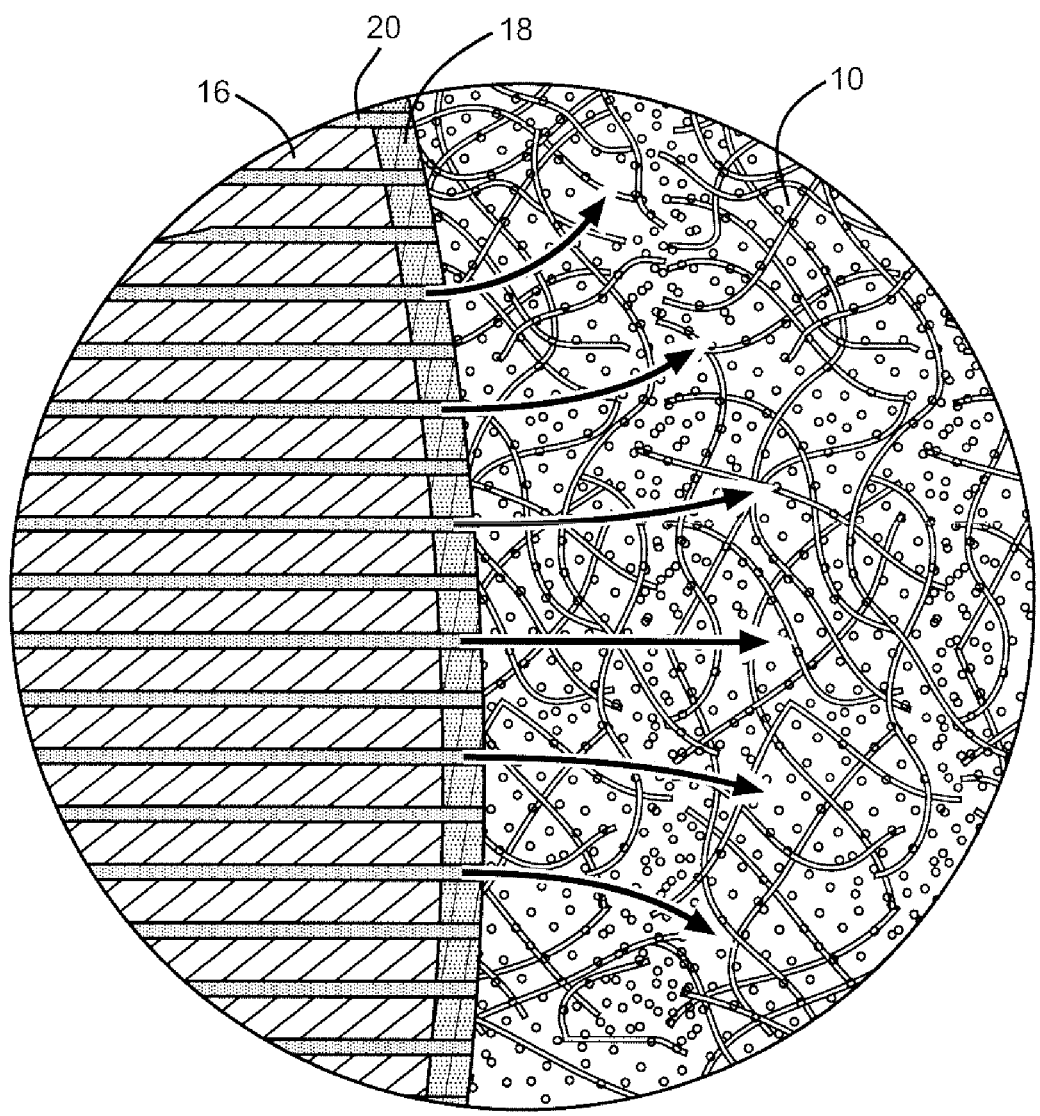
FIG. 4 is a cross-sectional view showing the interface between the stent and blood vessel 10 after deployment of the stent 12.

FIG. 4 shows the interface between the treated stent wire 14 and the blood vessel 10 after deployment of the stent 12 therein. Medication 20 residing in the capillary spaces of the columnar coating 16 is directed into the vessel 10 supported by the stent with the vessel tissue only contacting the biocompatible carbonaceous caps 18.

Figure 5:
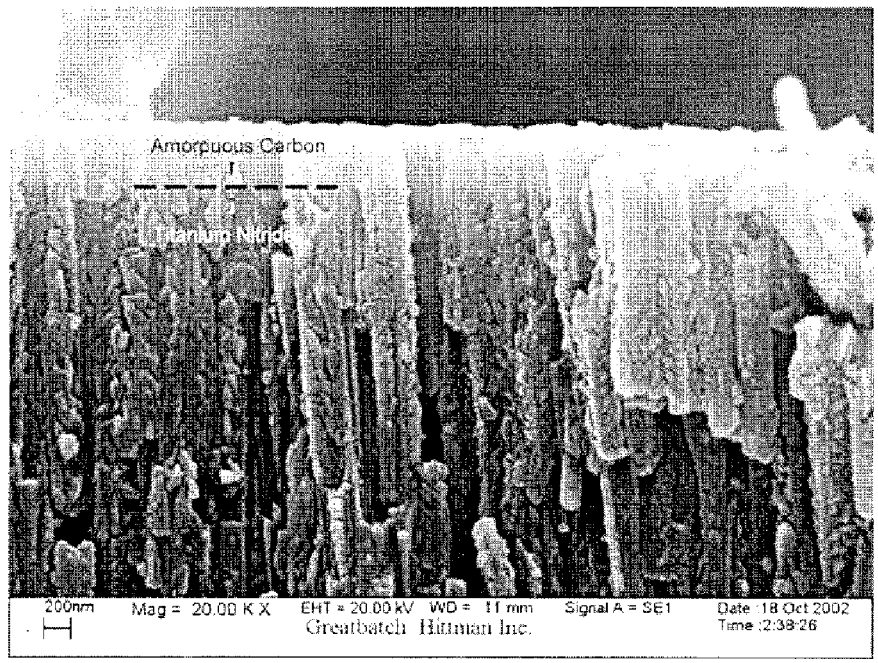
FIG. 5 is an SEM photograph of a fracture cross-section of a porous columnar titanium nitride coating with porous carbon caps.

It is to be appreciated that the schematics of FIGS. 1 to 4 do not illustrate the extremely high surface area present in the inter-columnar capillaries. FIG. 5 is a SEM photograph of a fracture cross-section of a porous columnar coating illustrating the volume of empty space therein and the internal surface roughness of the capillaries. In this case, the porous columnar coating consists of titanium nitride, which is widely used as a permanent implantable coating for bioelectrodes. Also visible in the photograph is the carbon cap on each individual titanium nitride column, comprising the outer 200 nm to 300 nm of the coating. Deposition of the carbon layer was done with the mandrel removed from the stent mesh. The mesh was fixtured to expose all surfaces of the stent to sputter flux. The stent was rotated in the sputter flux during deposition, which was done with DC sputtering of a carbon target in argon process gas. Typical conditions are 7 mTorr, 250 Watts, no bias. The result is a stent that presents a relatively thick, porous eluting layer containing therapeutic medication to the blood vessel wall, while presenting a smooth, hemocompatible face to the flowing blood.

Figure 6:
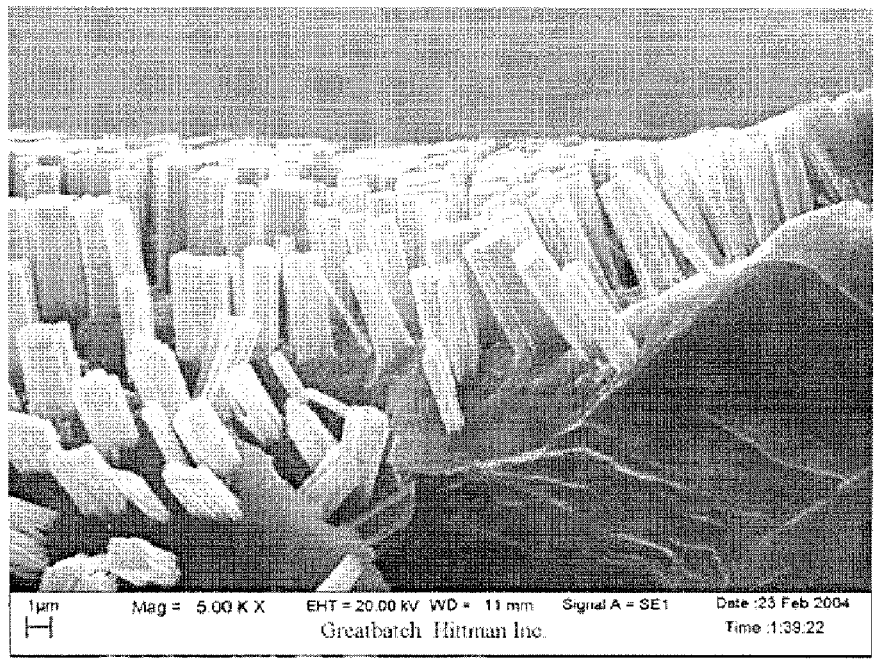
FIG. 6 is a SEM photograph showing sputtered columnar aluminum nitride adhering to a substrate that has been subjected to plastic deformation.

FIG. 6 illustrates adhesion of a porous columnar coating of aluminum nitride even after extensive plastic deformation of the substrate. Reactive DC sputtering was used. The process gas was pure nitrogen at a pressure of about 5.3 mTorr. Power was set at 250 W on a 3 inch diameter planar target with no bias. Deposition time was 4 hours.

In that respect, a further aspect of the invention relates to controlling the stress state of each column comprising the coating 16 supported on the stent wires 14. Fixturing the stent 12 on a mandrel (not shown) subjected to a sputter flux provides for coating the outside-facing surface 14A thereof with the columnar coating 16 while protecting the inside-facing surface 14B of the stent wire 14. Increasing the degree of expansion over the mandrel to higher levels, within the elastic limit of the stent wire 14, and sputtering in that expanded state, lessens the overall stress on the columnar coating 16 when the stent 12 is finally inserted and expanded in the blood vessel 10. Then, when the stent is plastically deformed upon deployment into the vasculature, the individual columns are less likely to delaminate from the wire substrate as their connection to the substrate is in a relatively less stressed state. The associated carbon caps 16 experience the same compression and tension stress forces because they essentially "ride" on the tips 16B of each column. This is illustrated in FIGS. 7A to 7E.

Figure 7A:
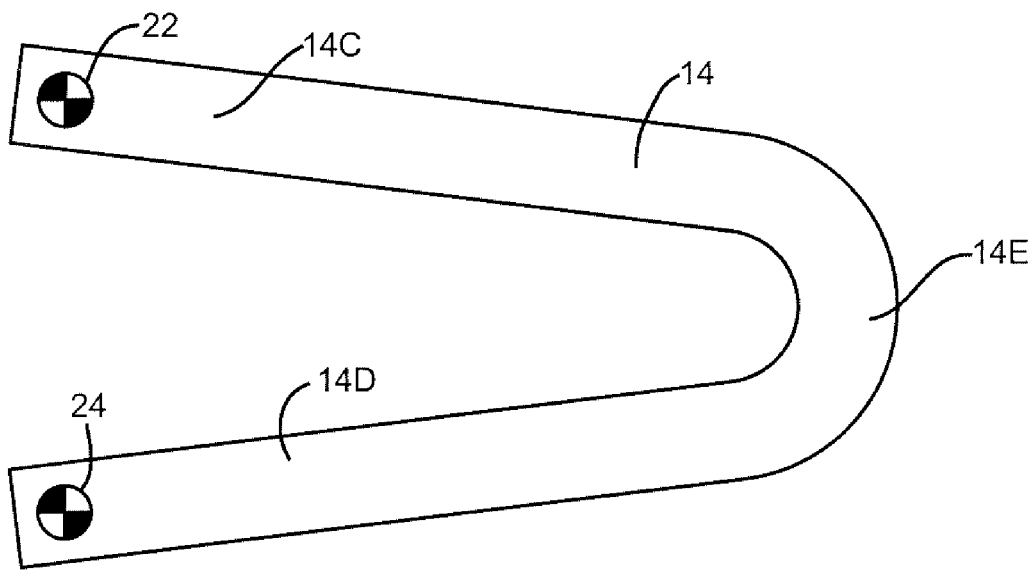
FIG. 7A is a schematic view of an unstrained stent wire 14 in a zero stress state.

FIG. 7A shows an unstrained stent wire 14. The wire has a generally elongate U-shape comprising spaced apart struts 14C and 14D joined together by a union portion 14E. Datum points 22 and 24 are indicated adjacent to the terminus of the respective struts 14C, 14D. In actuality the struts comprise a continuous structure such as a mesh and have no "terminus". When the stent is placed over a supporting mandrel (not shown), the distance between the datum points 22, 24 is increased, as indicated by the opposing directions of the respective vector arrows 22A and 24A in FIG. 7B. The stresses set up in the union portion 14E include both tension forces ($+\sigma_e$) and compression forces ($-\sigma_e$) within the elastic limits of the wire. The goal is to stress the union portion 14E of the wire 14 within its elastic limits so that the tension and compression strains create an opposite elastic pre-strain in the coating when the stent is removed from the mandrel. The struts 14C, 14D remain relatively unstressed.

Figure 7B:
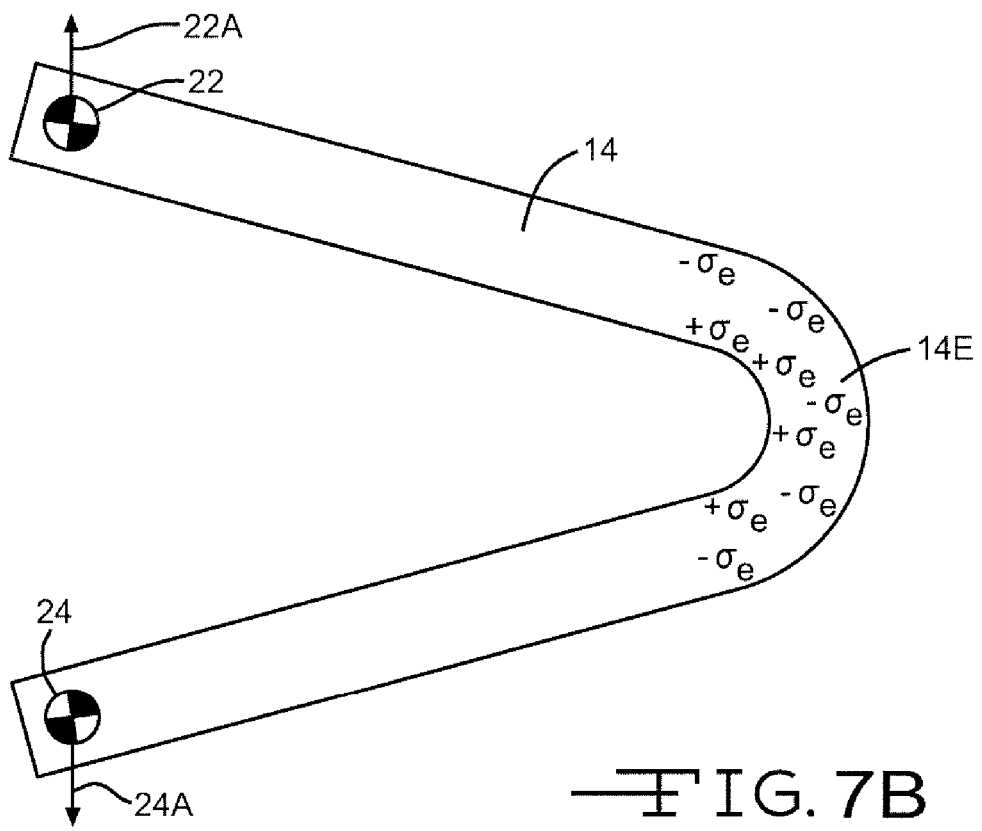
FIG. 7B is a schematic view of the stent wire 14 shown in FIG. 7A having been strained within its elastic limit and depicting the resulting tension and compression stress forces therein.
Figure 7C:
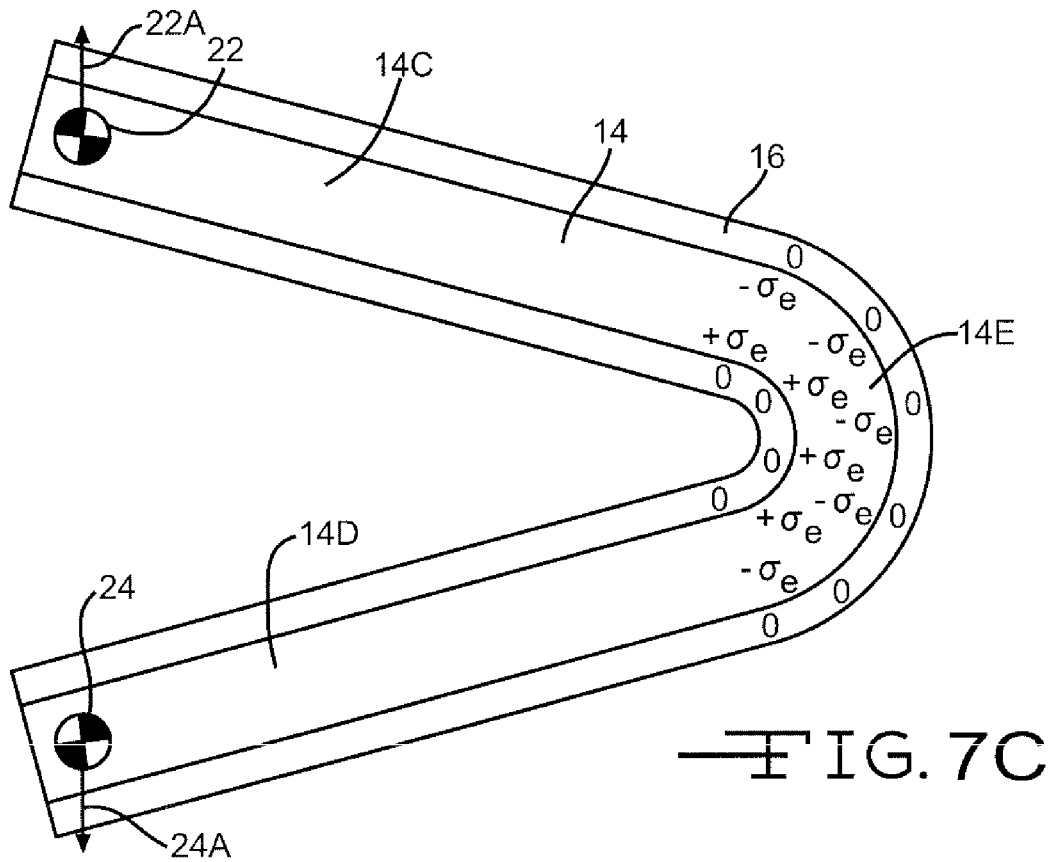
FIG. 7C is a schematic view of the stent wire 14 shown in FIG. 7B being elastically strained and provided with a columnar coating 16 that is an unstrained state.
Figure 7D:
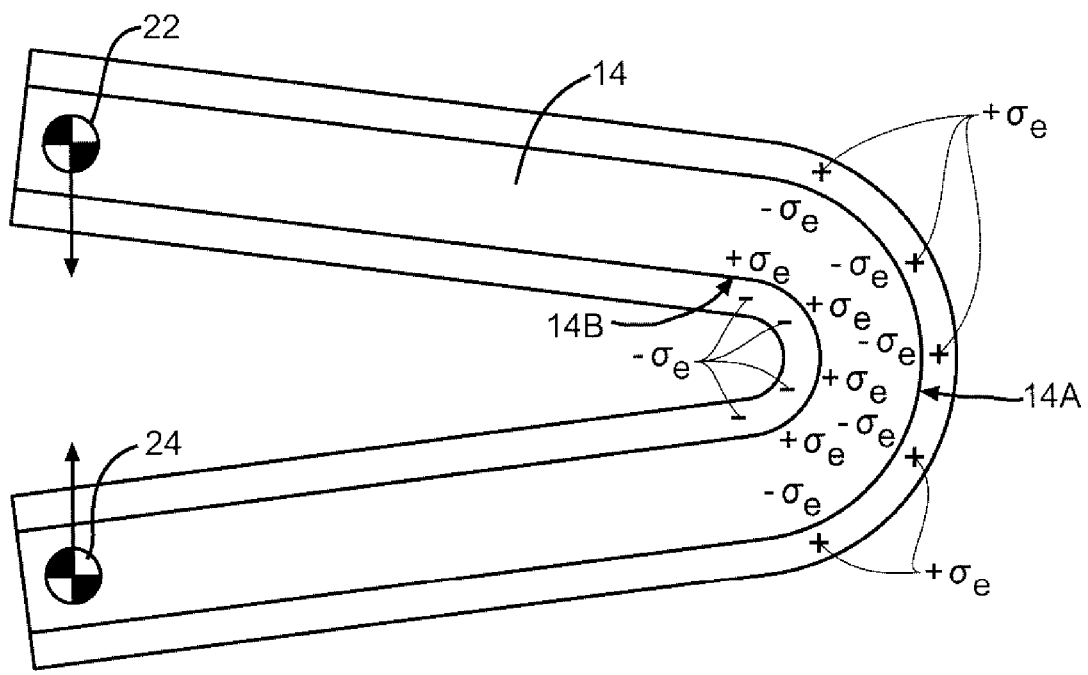
FIG. 7D is a schematic view of the stent wire 14 shown in FIG. 7C in a relaxed, unstrained state and depicting the resulting tension and compression stress forces in the columnar coating 16.

FIG. 7C shows the stent wire 14 in the same stressed state illustrated in FIG. 7B, but after the sputtered columnar coating 16 is applied. The columnar coating 16 is in a zero stress state. Then, as shown in FIG. 7D, when the stent is removed from the mandrel, it elastically springs back with the distance between the datum points 22, 24 being at or near to their original spacing shown in FIG. 7A. The columnar coating 16 is now in a stressed state opposite to that shown for the substrate in FIG. 7C. In that respect, the columnar coating 16 on the outside-facing surface 14A is in a tension state within the elastic limits of the wire coating material ($+\sigma_e$) while the columnar coating on the inside-facing surface 14B is in a compression state ($-\sigma_e$).

Figure 7E:
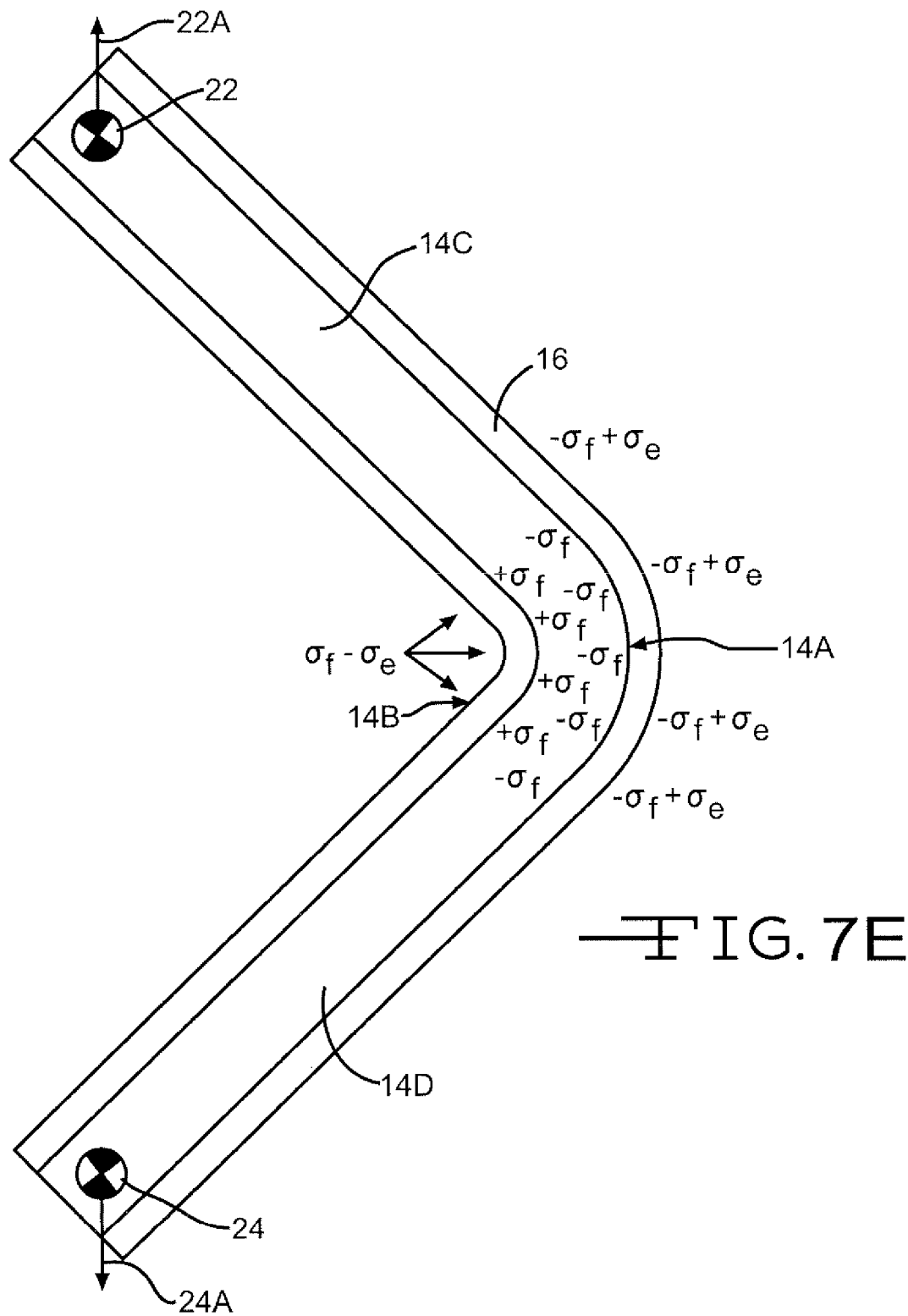
FIG. 7E is a schematic view of the stent wire 14 shown in FIG. 7C having been expanded past its elastic limit and depicting the resulting tension and compression stress forces in both the wire and the columnar coating 16.

In FIG. 7E, the wire 14 undergoes plastic deformation during the stent's expansion and placement in the vasculature. This is depicted by the opposing directions of the respective vector arrows 22A, 24A. In this final state, the stress in the coating 16 is the stress due to deformation of the wire surface at the union portion 14E minus the coating pre-stress, as shown in FIG. 7E. Therefore, the final tension ($-\sigma_f$) and compression ($+\sigma_f$) forces in the coating 16 are somewhat less than they would have been had the columnar coating been provided on the stent wire in a completely relaxed state in comparison to the actual stressed state the union portion 14E was in during the deposition process. The difference is the amount of elastic deformation in the union portion 14E of the stent wire 14 while the coating was being deposited (FIG. 7C).

The elastic limit of the stent wire 14 can be determined by placing the stent over increasingly larger diameter mandrels, until the spring back upon removal does not return the stent to its original dimension. Alternately, the film pre-stress can be achieved by using a nickel titanium shape memory alloy which can be made to assume the partially expanded configuration by heating in the sputter chamber.

Figure 8A:
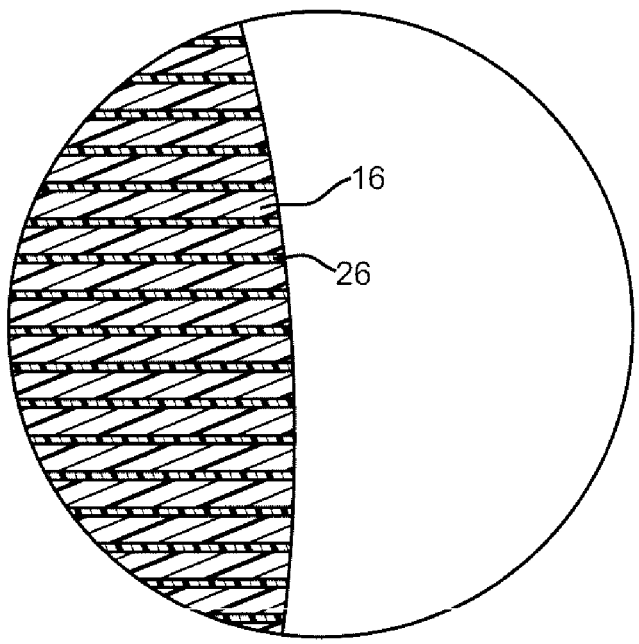
FIG. 8A is a cross-sectional view of a polymer 26 used as a reinforcing material between individual columns 16.

Another aspect of the invention is shown in FIG. 8A. This embodiment relates to the use of a polymer 26 that is provided with a medication and infused into the porous columnar coating 16 to improve biocompatibility while increasing coating strength and adhesion. Suitable polymers include (but are not limited to) polyurethane, silicone, polyesters, polycarbonate, polyethylene, polyvinyl chloride, polypropylene methylacrylate, para-xylylene.

Figure 8B:
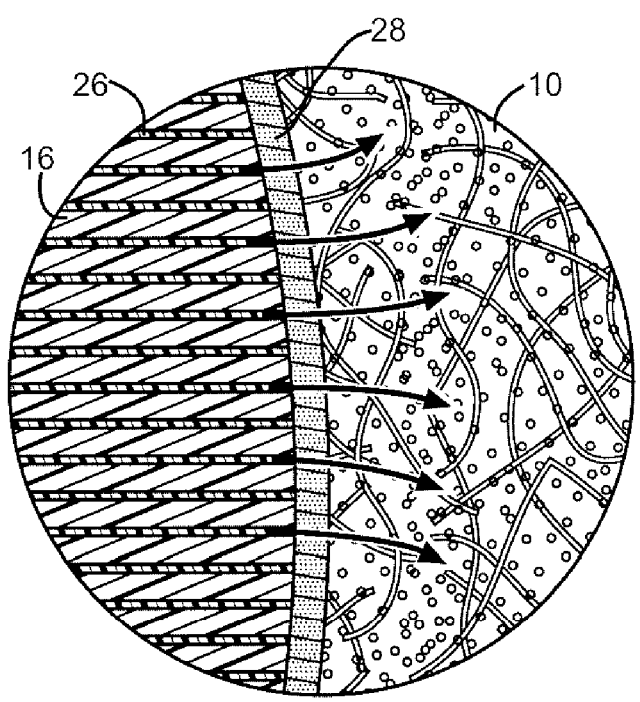
FIG. 8B is a cross-sectional view of the stent shown in FIG. 8A provided with a diffusion limiting polymeric coating 28.

As shown in FIG. 8B, a polymer 28 can also be used to moderate and control the diffusion of the medication from the capillaries of the porous coating 16 into the surrounding tissue. In that case the polymeric coating 28 is added to the porous layer after it is infused with the therapeutic medication.

Because the process coats all surfaces of the stent, it allows selection from a wider range of substrate materials, including those which improved radiopacity characteristics. This is an important consideration for locating the stent correctly during placement in the vasculature.

It is appreciated that various modifications to the invention concepts described herein may be apparent to those of ordinary skill in the art without departing from the scope of the present invention as defined by the appended claims.

What is claimed is:

1. A device comprising a biocompatible coating for contact with body tissue, the device comprising:
   a) a substrate;
   b) an intermediate coating of a metal or a ceramic adhered to the substrate and comprising a plurality of discrete columnar structures, each of the columns having a sidewall extending between a proximal end adhered to the substrate and a distal end spaced therefrom, wherein the sidewalls of immediately adjacent columns do not contact each other to thereby provide an area of the substrate between adjacent columns that is not contacted by the intermediate coating serving as porosity between the columns; and
   c) a cap of a carbon-containing material provided on the distal end of each of the plurality of columnar structures.

2. The device of claim 1 wherein the intermediate coating is selected from the group consisting of carbides, oxides, nitrides, oxynitrides, and carbonitrides of titanium, boron, aluminum, calcium, gold, hafnium, iridium, molybdenum, niobium, platinum, rhenium, ruthenium, silicon, silver, tantalum, titanium, tungsten, yttrium, zirconium.

3. The device of claim 1 wherein the carbon-containing material is selected from an amorphous carbon and a diamond-like carbon.

4. The device of claim 1 wherein the intermediate coating is adhered to the substrate and the carbon-containing material is provided as the cap on the distal end of each of the plurality of columnar structures by one of the deposition techniques selected from the group consisting of sputtering, chemical vapor deposition, pulsed laser deposition, reactive evaporation, and as a thermal spray.

5. The device of claim 1 wherein the plurality of columnar structures comprising the intermediate coating each have a length of about 0.1 μm to about 20 μm.

6. The device of claim 1 wherein the carbon-containing material has a thickness of about 0.05 μm to about 2.0 μm.

7. A device comprising a biocompatible coating for contact with body tissue, the device comprising:
   a) a substrate;
   b) an intermediate coating of titanium nitride adhered to the substrate and comprising a plurality of discrete columnar structures, each of the columns having a sidewall extending between a proximal end adhered to the substrate and a distal end spaced therefrom, wherein the sidewalls of immediately adjacent titanium nitride columns do not contact each other to thereby provide an area of the substrate between adjacent columns that is not contacted by the intermediate coating serving as porosity adapted for receiving an elutable material between the columns;
   c) a cap of a carbon-containing material provided on the distal end of each of the plurality of columnar structures.

8. The device of claim 7 wherein the carbon-containing material is selected from an amorphous carbon and a diamond-like carbon.

9. The device of claim 7 wherein the intermediate coating is adhered to the substrate and the carbon-containing material is provided as the cap on the distal end of each of the plurality of columnar structures by one of the deposition techniques selected from the group consisting of sputtering, chemical vapor deposition, pulsed laser deposition, reactive evaporation, and as a thermal spray.

10. The device of claim 7 wherein the plurality of columnar structures comprising the intermediate coating each have a length of about 0.1 μm to about 20 μm.

11. The device of claim 7 wherein the carbon-containing material has a thickness of about 0.05 μm to about 2.0 μm.

12. A device comprising a biocompatible coating for contact with body tissue, the device comprising:
   a) a substrate;
   b) an intermediate coating of a metal or a ceramic adhered, to the substrate and comprising a plurality of discrete columnar structures, each of the columns having a sidewall extending between a proximal end adhered to the substrate and a distal end spaced therefrom, wherein the sidewalls of immediately adjacent columns do not contact each other to thereby provide an area of the substrate between adjacent columns that is not contacted by the intermediate coating serving as porosity adapted for receiving an elutable material between the columns;
   c) a cap of a carbon-containing material provided on the distal end of each of the plurality of columnar structures; and
   d) wherein stress levels between immediately adjacent columnar structures are sufficiently within elastic limits of the substrate such that delamination upon expansion of the substrate is substantially precluded.

13. The device of claim 12 wherein the intermediate coating is selected from the group consisting of carbides, oxides, nitrides, oxynitrides, and carbonitrides of titanium, boron, aluminum, calcium, gold, hafnium, iridium, molybdenum, niobium, platinum, rhenium, ruthenium, silicon, silver, tantalum, titanium, tungsten, yttrium, zirconium.

14. The device of claim 12 wherein the carbon-containing material is selected from an amorphous carbon and a diamond-like carbon.

15. The device of claim 12 wherein the intermediate coating is adhered to the substrate and the carbon-containing material is provided as the cap on the distal end of each of the plurality of columnar structures by one of the deposition techniques selected from the group consisting of sputtering, chemical vapor deposition, pulsed laser deposition, reactive evaporation, and as a thermal spray.

16. The device of claim 12 wherein the plurality of columnar structures comprising the intermediate coating each have a length of about 0.1 μm to about 20 μm.

17. The device of claim 12 wherein the carbon-containing material has a thickness of about 0.05 μm to about 2.0 μm.

* * * * *